(12) United States Patent
Stewart et al.

(10) Patent No.: US 11,701,169 B2
(45) Date of Patent: Jul. 18, 2023

(54) CARDIAC PULSED FIELD ABLATION

(71) Applicant: Medtronic, Inc., Minneapolis, MN (US)

(72) Inventors: Mark T. Stewart, Lino Lakes, MN (US); Steven J. Fraasch, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 417 days.

(21) Appl. No.: 16/707,260

(22) Filed: Dec. 9, 2019

(65) Prior Publication Data

US 2020/0107879 A1   Apr. 9, 2020

Related U.S. Application Data

(63) Continuation of application No. 15/228,406, filed on Aug. 4, 2016, now Pat. No. 10,531,914.

(60) Provisional application No. 62/201,622, filed on Aug. 6, 2015.

(51) Int. Cl.
*A61B 18/12* (2006.01)
*A61B 18/14* (2006.01)
*A61N 1/32* (2006.01)
*A61B 18/00* (2006.01)

(52) U.S. Cl.
CPC ...... *A61B 18/1492* (2013.01); *A61B 18/1206* (2013.01); *A61N 1/327* (2013.01); *A61B 2018/0075* (2013.01); *A61B 2018/00351* (2013.01); *A61B 2018/00577* (2013.01); *A61B 2018/00613* (2013.01); *A61B 2018/00761* (2013.01); *A61B 2018/00767* (2013.01);
(Continued)

(58) Field of Classification Search
CPC ...... A61B 18/1206; A61B 2018/00351; A61B 2018/00577; A61B 2018/00613; A61B 2018/0075; A61B 2018/00761; A61B 2018/00767; A61B 2018/00839; A61B 2018/126; A61B 2018/1407; A61N 1/327
See application file for complete search history.

(56) References Cited

U.S. PATENT DOCUMENTS 5,836,990 A   11/1998  Li
6,463,330 B1  10/2002  Rabinovitch et al.
7,742,809 B2   6/2010  Sigg et al.
(Continued)

FOREIGN PATENT DOCUMENTS

CN   103442631 A   12/2013
CN   103781433 A    5/2014
(Continued)

OTHER PUBLICATIONS

Greg Mcallister, et al., Medtronic Pulsed Field Ablation, IP Review Sep. 27, 2016, 33 pages.
(Continued)

*Primary Examiner* — Michael F Peffley
(74) *Attorney, Agent, or Firm* — Michael Best & Friedrich LLP (57) ABSTRACT

A method for ablating tissue by applying at least one pulse train of pulsed-field energy. The method includes delivering a pulse train of energy having a predetermined frequency to cardiac tissue, the pulse train including at least 60 pulses, an inter-phase delay between 0 µs and 5 µs, an inter-pulse delay of at least 5 µs, and a pulse width of 5 µs.

18 Claims, 7 Drawing Sheets

(52) U.S. Cl.
CPC ............. *A61B 2018/00839* (2013.01); *A61B 2018/126* (2013.01); *A61B 2018/1407* (2013.01)

(56) References Cited

U.S. PATENT DOCUMENTS

| | | | |
|---|---|---|---|
| 8,221,411 B2* | 7/2012 | Francischelli | A61B 18/1492 606/41 |
| 8,465,484 B2* | 6/2013 | Davalos | A61B 18/1477 604/20 |
| 8,926,606 B2 | 1/2015 | Davalos et al. | |
| 9,113,911 B2 | 8/2015 | Sherman | |
| 2003/0204161 A1 | 10/2003 | Ferek-Petric | |
| 2004/0054391 A1 | 3/2004 | Wildon | |
| 2010/0023004 A1 | 1/2010 | Francischelli et al. | |
| 2010/0261994 A1* | 10/2010 | Davalos | A61B 18/1477 600/407 |
| 2010/0305462 A1 | 12/2010 | Callas et al. | |
| 2012/0220998 A1 | 8/2012 | Long | |
| 2012/0220999 A1* | 8/2012 | Long | A61B 18/1477 606/41 |
| 2013/0030425 A1 | 1/2013 | Stewart et al. | |
| 2013/0030430 A1* | 1/2013 | Stewart | A61B 18/1492 606/41 |
| 2013/0218157 A1 | 8/2013 | Callas et al. | |

FOREIGN PATENT DOCUMENTS

| | | |
|---|---|---|
| CN | 104688333 A | 6/2015 |
| CN | 104812297 A | 7/2015 |
| WO | 2015103574 A1 | 7/2015 |
| WO | WO 2015/103574 * | 7/2015 |
| WO | 2015171921 A2 | 11/2015 |
| WO | 2015171921 A3 | 11/2015 |

OTHER PUBLICATIONS

International Search Report and Written Opinion dated Feb. 12, 2016, for corresponding International Application No. PCT/US2016/045536; International Filing Date: Aug. 4, 2016 consisting of 9 pages.

Alenka Macek Lebar, et al., Inter-Pulse Interval Between Rectangular Voltage Pulses Affects Electroporation Threshold of Artificial Lipid Bilayers, IEEE Transactions on Nanobioscience, vol. 1, No. 3, Sep. 2002.

Paul J. Canatella, et al., Quantitative Study of Electroporation-Mediated Molecular Uptake and Cell Viability, Biophysical Journal, vol. 80, Feb. 2001, 755-764.

Gorazd Pucihar, et al., Equivalent Pulse Parameters for Electroporation, IEEE Transactions on Biomedical Engineering, vol. 58. No. 11, Nov. 2011.

China National Intellectual Property Administration, Notice on the First Office Action and Search Report, for corresponding Chinese Application No. 201680046257.8, dated Jul. 17, 2020, 21 pages.

European Patent Office, Summons to Attend Oral Proceedings pursuant to Rule 115(1) EPC, for corresponding European Application No. 16 753 529.3-1122, dated Jan. 10, 2020, 5 pages.

Chinese Patent Office Supplementary Search Report for Application No. 2016800462578 dated May 20, 2021 (1 page).

* cited by examiner

CARDIAC PULSED FIELD ABLATION

CROSS-REFERENCE TO RELATED APPLICATION

This application is a continuation of U.S. application Ser. No. 15/228,406, filed Aug. 4, 2016 and is related to and claims priority to U.S. Provisional Patent Application Ser. No. 62/201,622, filed Aug. 6, 2015, entitled CARDIAC PULSED FIELD ABLATION, the entirety of which is incorporated herein by reference.

STATEMENT REGARDING FEDERALLY SPONSORED RESEARCH OR DEVELOPMENT n/a

TECHNICAL FIELD

The present invention relates to a method and system for treating tissue with electroporation or pulsed-field ablation.

BACKGROUND

There are many medical treatments that involve instances of cutting, ablating, coagulating, destroying, or otherwise changing the physiological properties of tissue. These techniques can be used beneficially to change the electrophysiological properties of tissue, such as those associated with cardiac arrhythmias or other electrophysiological abnormalities. In particular, normal sinus rhythm of the heart begins with the sinoatrial node ("SA node") generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is next delivered via the atrioventricular node ("AV node") and the bundle of HIS to myocardial tissue cells of the ventricles. The depolarization of cells propagates across the ventricles, causing the ventricles to contract. This conduction system results in the described, organized sequence of myocardial contraction leading to a normal heartbeat.

Sometimes, anatomical obstacles such as fibrosis, fibrotic scar, or uneven distribution of refractoriness of cardiac myocytes in certain parts of the heart in the atria or ventricles can lead to aberrant conductive pathways in heart tissue that disrupt the normal path of depolarization events. These anatomical obstacles or "conduction blocks" can cause the electrical impulse to degenerate into several circulating wavelets that circulate about the obstacles. The aberrant conductive pathways create abnormal, irregular, and sometimes life-threatening heart rhythms called arrhythmias. An arrhythmia can take place in the atria, for example, as in atrial tachycardia, atrial fibrillation ("AF"), or atrial flutter. The arrhythmia can also take place in the ventricle, for example, as in ventricular tachycardia. Additionally, there may be ectopic sites within the heart that produce premature activations from such tissue sites, producing arrhythmogenic conduction patterns.

One approach to treating an arrhythmia includes creating one or more lesions that compartmentalize the aberrant pathway and direct electrical conduction along selected pathways to promote organized signal conduction, while also isolating AF triggers from connecting with the atria. Often, the application of energy is used to destroy cells at the ablation site while leaving the surrounding structures of the organ largely intact. Radiofrequency ("RF") energy and cryogenic cooling have been found to be highly viable in this regard, and are commonly employed. Other ablative techniques include the application of ultrasound, microwave, laser, cytotoxic agents, etc.

However, there may be potential drawbacks associated with the application of RF energy. One such potential drawback is that the application of RF energy to a target tissue site may have effects on non-target tissue. For example, the application of RF energy to atrial wall tissue may cause collateral damage in the esophagus or phrenic nerve, which are typically located proximate the heart. Further, RF ablation procedures may require an extended period of treatment time before the arrhythmia is corrected, which can increase the likelihood of collateral damage to non-target tissue or the occurrence of tissue charring, which could result in an embolic event.

SUMMARY

The present invention advantageously provides a method and system for treating cardiac tissue. The method includes delivering a pulse train of energy having a predetermined frequency to cardiac tissue. The pulse train including at least 60 pulses, an inter-phase delay between 0 µs and 5 µs, an inter-pulse delay of at least 5 µs, and a pulse width between 1 and 5 µs.

In another aspect of this embodiment, the pulse train of energy has a voltage between 300V and 4000V and wherein the predetermined frequency is approximately 1 kHz.

In another aspect of this embodiment, the inter-pulse delay is 800 µs.

In another aspect of this embodiment, the pulse train of energy is initiated between 70 ms and 100 ms after onset of an R-wave.

In another aspect of this embodiment, the pulse train of energy is gated to initiate the delivery of the pulse train radiofrequency energy at the end of an S-wave.

In another aspect of this embodiment, the pulse train of energy may be delivered to a plurality of cardiac treatment sites, and the method further includes delivering the pulse train of energy four times at each of the plurality of treatment sites.

In another aspect of this embodiment, the method further includes positioning a medical device proximate the cardiac tissue to be treated, the medical device including a distal electrode array having a plurality of electrodes, each electrode having a polarity that is different than each adjacent electrode, and where the pulse train of energy is delivered from the distal electrode array.

In another aspect of this embodiment, the pulse train of energy is delivered in bipolar mode.

In another aspect of this embodiment, the pulse train of energy includes biphasic pulses.

In another aspect of this embodiment, the biphasic pulses are delivered at a plurality of voltage amplitudes.

In another aspect of this embodiment, the plurality of voltage amplitudes includes a first amplitude and a second amplitude, the second amplitude being higher than the first amplitude, and wherein the biphasic pulses delivered at the first amplitude are delivered at a higher frequency than the biphasic pulses delivered at the second amplitude.

In another embodiment, the system includes a generator configured to deliver at least one pulse train of energy at a predetermined frequency. Each pulse train of energy includes at least 60 pulses, an inter-phase delay of between 0 µs and 5 µs, an inter-pulse delay of at least 5 µs, a pulse width of 1-15 µs, and a voltage between 300V and 4000V. The generator further includes a processor configured to control the delivery of the at least one pulse train based on a measured patient parameter.

In another aspect of this embodiment, the system further includes a medical device in electrical communication with the generator, the medical device having a plurality of electrodes, each electrode having a polarity that is different than each adjacent electrode, the at least one pulse train of energy being delivered in bipolar mode from the plurality of electrodes.

In another aspect of this embodiment, the system further includes ECG electrodes couplable to the generator and in communication with the processor, the ECG electrodes being configured to measure electrical waveforms generated by a patient's heart, and wherein the measured patient parameter is measured by the ECG electrodes.

In another aspect of this embodiment, the inter-pulse delay is 800 µs, and wherein the predetermined frequency is approximately 1 kHz.

In another aspect of this embodiment, the measured patient parameter includes the detection of the onset of an R-wave, and wherein the generator is configured to initiate the pulse train of energy between 70 ms and 100 ms after onset of an R-wave measured.

In another aspect of this embodiment, the measured patient parameter includes the detection of the onset of an S-wave, and wherein the pulse train of energy is gated by the processor to initiate the delivery of the pulse train of energy at the end of an S-wave.

In another aspect of this embodiment, the generator is configured to initiate the pulse train of energy after a predetermined delay following the delivery of a 5-10V, low amplitude monophasic pacing pulse from the plurality of electrodes, the pacing pulse being 0.5 ms in duration and being at least one of synchronous and asynchronous.

In another aspect of this embodiment, the low amplitude monophasic pacing pulse is the last pulse in a series of pacing pulse delivered by the generator.

In another aspect of this embodiment, the pulse train of energy includes biphasic pulses, and wherein the generator is configured to deliver the biphasic pulses at a plurality of voltage amplitudes.

In another aspect of this embodiment, the plurality of voltage amplitudes includes a first amplitude and a second amplitude, the second amplitude being higher than the first amplitude, and wherein the biphasic pulses delivered at the first amplitude are delivered at a higher frequency than the biphasic pulses delivered at the second amplitude.

In yet another embodiment, the method includes positioning a medical device proximate cardiac tissue to be treated. The medical device has a plurality of electrodes, each electrode having a polarity that is different than each adjacent electrode. An electrocardiogram is measured from ECG electrodes, the measured electrocardiogram includes a QRS waveform. A biphasic pulse train of energy, at a frequency of approximately 1 kHz, is delivered between adjacent electrodes of the plurality of electrodes to the cardiac tissue to be treated between 70 ms and 100 ms after onset of an R-wave measured by the ECG electrodes, the pulse train of energy includes a plurality of voltage amplitudes, at least 60 pulses, an inter-phase delay between 0 µs and 5 µs, an inter-pulse delay of at least 400 µs, a pulse width of 1-15 µs, and a voltage between 300V and 4000V. The plurality of voltage amplitudes includes a first amplitude and a second amplitude, the second amplitude being higher than the first amplitude, the biphasic pulses delivered at the first amplitude are delivered at a higher frequency than the biphasic pulses delivered at the second amplitude.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
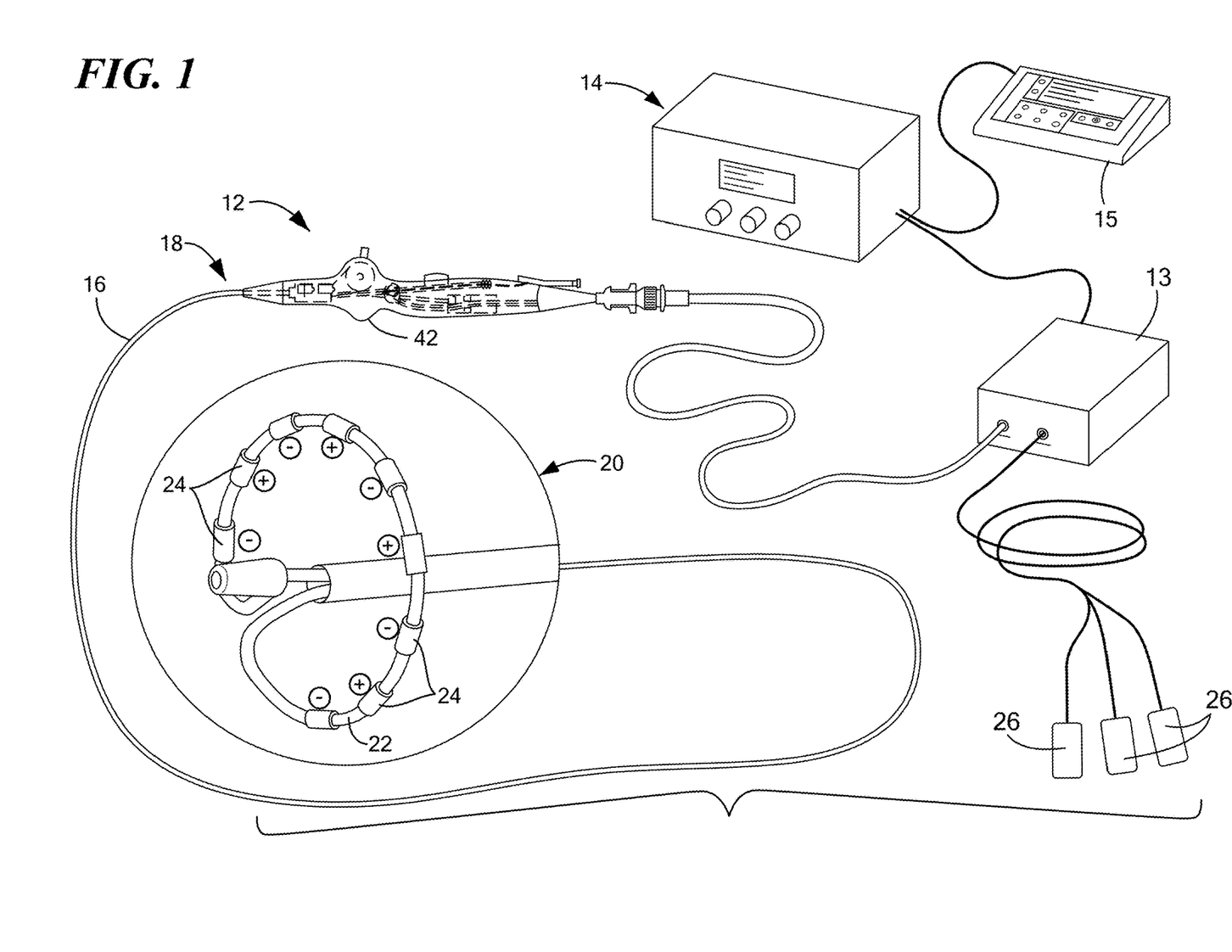
FIG. 1 shows an exemplary ablation system including a pulsed-field ablation device having an exemplary distal curvilinear electrode array portion.

The present application provides methods and systems for diagnosing and/or treating undesirable physiological or anatomical tissue regions, such as those contributing to aberrant electrical pathways in the heart. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled directly to an energy supply, for example, a pulse field ablation generator 14 including an energy control, delivering and monitoring system or indirectly through a catheter electrode distribution system 13. A remote controller 15 may further be included in communication with the generator for operating and controlling the various functions of the generator 14. The medical device 12 may generally include one or more diagnostic or treatment regions for energetic, therapeutic and/or investigatory interaction between the medical device 12 and a treatment site. The treatment region(s) may deliver, for example, pulsed electroporation energy to a tissue area in proximity to the treatment region(s).

The medical device 12 may include an elongate body 16 passable through a patient's vasculature and/or positionable proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16. The distal portion 20 may generally define the one or more treatment region(s) of the medical device 12 hat are operable to monitor, diagnose, and/or treat a portion of a patient. The treatment region(s) may have a variety of configurations to facilitate such operation. In the case of purely bipolar pulsed field delivery, distal portion 20 includes electrodes that form the bipolar configuration for energy delivery. In an alternate configuration, a plurality of the electrodes 24 may serve as one pole while a second device containing one or more electrodes (not pictured) would be placed to serve as the opposing pole of the bipolar configuration. For example, as shown in FIG. 1, the distal portion 20 may include an electrode carrier arm 22 that is transitionable between a linear configuration and an expanded configuration in which the carrier arm 22 has an arcuate or substantially circular configuration. The carrier arm 22 may include the plurality of electrodes 24 (for example, nine electrodes 24, as shown in FIG. 1) that are configured to deliver pulsed-field energy. Further, the carrier arm 22 when in the expanded configuration may lie in a plane that is substantially orthogonal to the longitudinal axis of the elongate body 16. The planar orientation of the expanded carrier arm 22 may facilitate ease of placement of the plurality of electrodes 24 in contact with the target tissue. Alternatively, the medical device 12 may be have a linear configuration with the plurality of electrodes 24. For example, the distal portion 20 may include six electrodes 24 linearly disposed along a common longitudinal axis.

The generator 14 may include processing circuitry including a first processor 17 in communication with one or more controllers and/or memories containing software modules containing instructions or algorithms to provide for the automated operation and performance of the features, sequences, calculations, or procedures described herein. The system 10 may further include three or more surface ECG electrodes 26 on the patient in communication with the generator 14 through the catheter electrode distribution box 13 to monitor the patient's cardiac activity for use in determining pulse train delivery timing at the desired portion of the cardiac cycle, for example, during the ventricular refractory period. In addition to monitoring, recording or otherwise conveying measurements or conditions within the medical device 12 or the ambient environment at the distal portion of the medical device 12, additional measurements may be made through connections to the multi-electrode catheter including for example temperature, electrode-tissue interface impedance, delivered charge, current, power, voltage, work, or the like in the generator 14 and/or the medical device 12. The surface ECG electrodes 26 may be in communication with the generator 14 for initiating or triggering one or more alerts or therapeutic deliveries during operation of the medical device 12. Additional neutral electrode patient ground patches (not pictured) may be employed to evaluate the desired bipolar electrical path impedance, as well as monitor and alert the operator upon detection of inappropriate and/or unsafe conditions, which include, for example, improper (either excessive or inadequate) delivery of charge, current, power, voltage and work performed by the plurality of electrodes 24; improper and/or excessive temperatures of the plurality of electrodes 24; improper electrode-tissue interface impedances; improper and/or inadvertent electrical connection to the patient prior to delivery of high voltage energy by delivering one or more low voltage test pulses to evaluate the integrity of the tissue electrical path.

The generator 14 may include an electrical current or pulse generator having a plurality of output channels, with each channel coupled to an individual electrode of the plurality of electrodes 24 or multiple electrodes of the plurality of electrodes 24 of the medical device 12. The generator 14 may be operable in one or more modes of operation, including for example: (i) bipolar energy delivery between at least two electrodes 24 or electrically-conductive portions of the medical device 12 within a patient's body, (ii) monopolar or unipolar energy delivery to one or more of the electrodes or electrically-conductive portions on the medical device 12 within a patient's body and through either a second device within the body (not shown) or a patient return or ground electrode (not shown) spaced apart from the plurality of electrodes 24 of the medical device 12, such as on a patient's skin or on an auxiliary device positioned within the patient away from the medical device 12, for example, and (iii) a combination of the monopolar and bipolar modes.

The generator 14 may provide electrical pulses to the medical device 12 to perform an electroporation procedure to cardiac tissue or other tissues within the body, for example, renal tissue, airway tissue, and organs or tissue within the cardiothoracic space. "Electroporation" utilizes high amplitude pulses to effectuate a physiological modification (i.e., permeabilization) of the cells to which the energy is applied. Such pulses may preferably be short (e.g., nanosecond, microsecond, or millisecond pulse width) in order to allow application of high voltage, high current (for example, 20 or more amps) without long duration of electrical current flow that results in significant tissue heating and muscle stimulation. In particular, the pulsed energy induces the formation of microscopic pores or openings in the cell membrane. Depending upon the characteristics of the electrical pulses, an electroporated cell can survive electroporation (i.e., "reversible electroporation") or die (i.e., irreversible electroporation, "IEP"). Reversible electroporation may be used to transfer agents, including large molecules, into targeted cells for various purposes, including alteration of the action potentials of cardiac myocyctes.

The generator 14 may be configured and programmed to deliver pulsed, high voltage electric fields appropriate for achieving desired pulsed, high voltage ablation (or pulsed field ablation). As a point of reference, the pulsed, high voltage, non-radiofrequency, ablation effects of the present disclosure are distinguishable from DC current ablation, as well as thermally-induced ablation attendant with conventional RF techniques. For example, the pulse trains delivered by generator 14 are delivered at a frequency less than 3 kHz, and in an exemplary configuration, 1 kHz, which is a lower frequency than radiofrequency treatments. The pulsed-field energy in accordance with the present disclosure is sufficient to induce cell death for purposes of completely blocking an aberrant conductive pathway along or through cardiac tissue, destroying the ability of the so-ablated cardiac tissue to propagate or conduct cardiac depolarization waveforms and associated electrical signals.

The plurality of electrodes 24 may also perform diagnostic functions such as collection of intracardiac electrograms (EGM) as well as performing selective pacing of intracardiac sites for diagnostic purposes. In one configuration, the measured ECG signals, are transferred from the catheter electrode energy distribution system 13 to an EP recording system input box (not shown) which is included with generator 14. The plurality of electrodes 24 may also monitor the proximity to target tissues and quality of contact with such tissues using impedance based measurements with connections to the catheter electrode energy distribution system 13. The catheter electrode energy distribution system 13 may include high speed relays to disconnect/reconnected specific electrode 24 from the generator 14 during therapies. Immediately following the pulsed energy deliveries, the relays reconnect the electrodes 24 so they may be used for diagnostic purposes.

Figure 4:
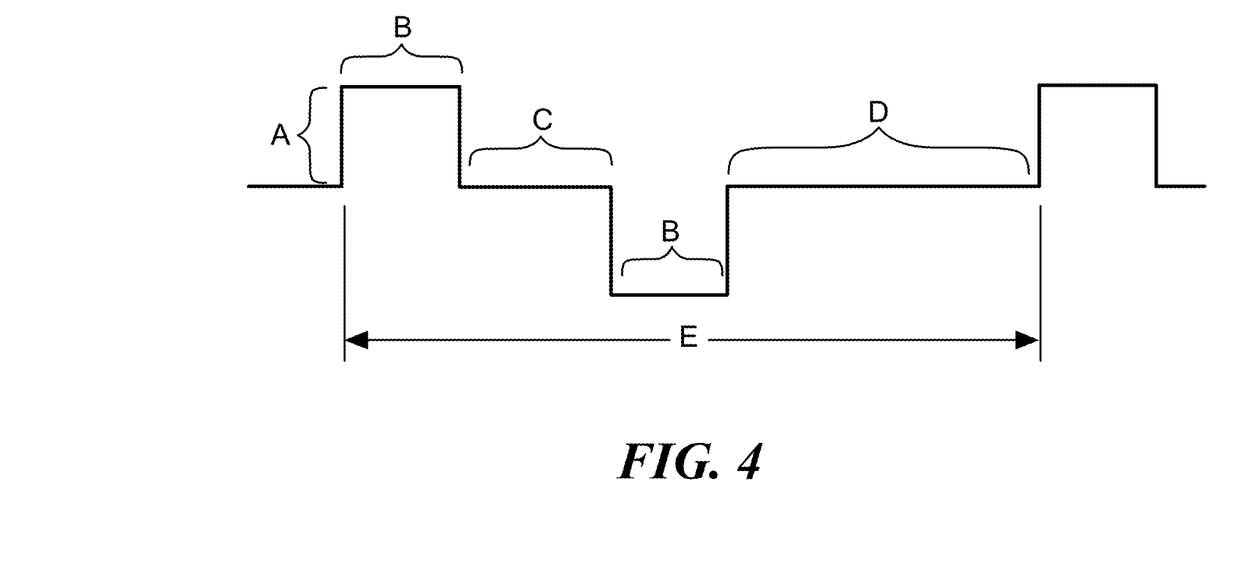
FIG. 4 shows pulse properties of a pulsed-field ablation scheme.
Figure 6:
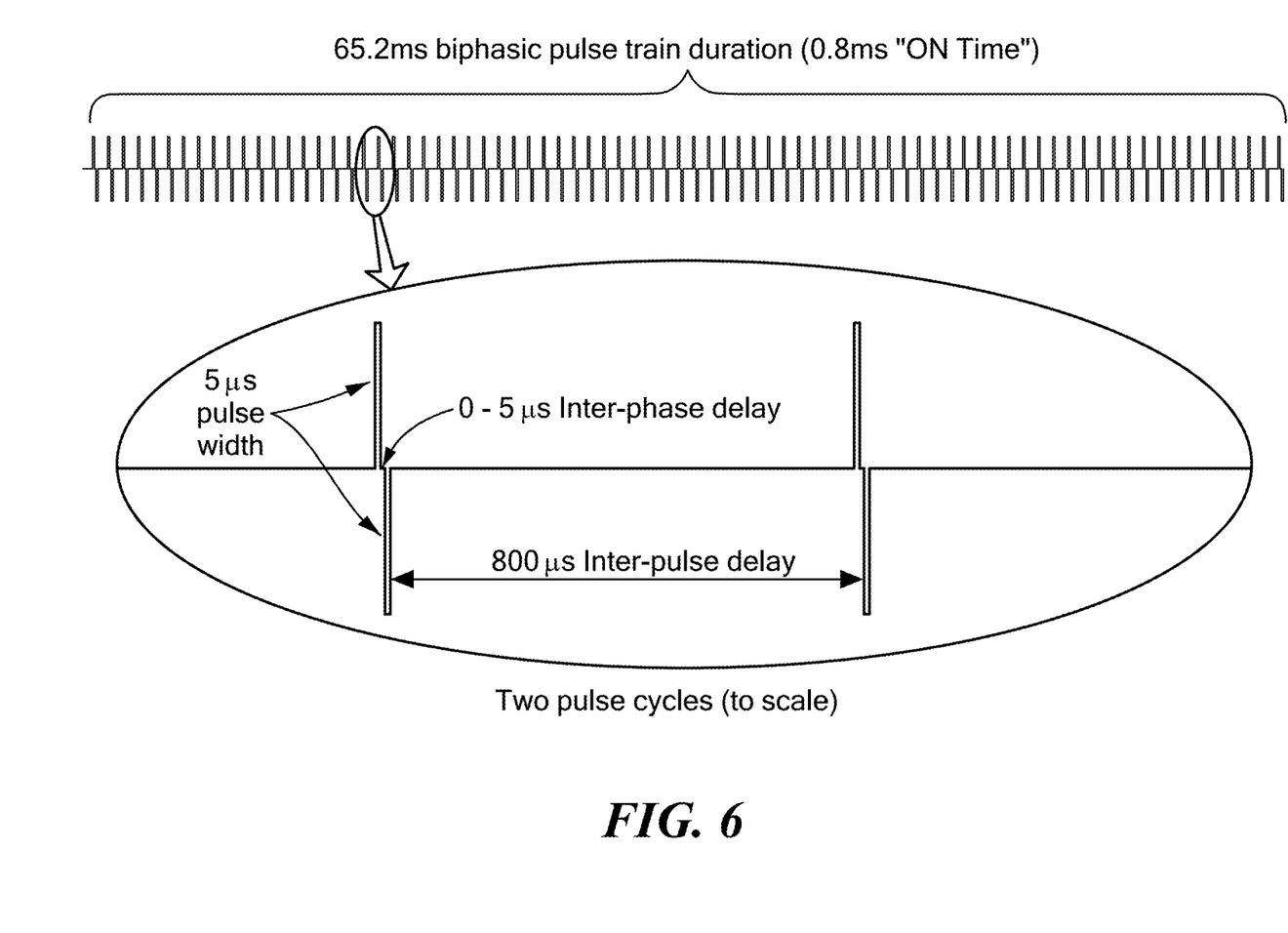
FIG. 6 shows a pulsed-field ablation pulse train including 80 pulses with a 5 µs inter-phase delay, a 5 µs pulse width, and an 800 µs inter-pulse delay, with an inset showing two pulse cycles.

Referring now to FIG. 4, the plurality of electrodes 24 may deliver therapeutic biphasic pulses having a preprogrammed pattern and duty cycle. For example, each pulse cycle may include an applied voltage amplitude A, a pulse width B (in μs), an inter-phase delay C (in μs), an inter-pulse delay D (in μs), and a pulse cycle length E. In an exemplary configuration, the pulse width B may be 1-15 μs, the inter-phase delay C may be 0-4 μs, the inter-pulse delay D may be 5-30,000 μs, the pulse train may include 20-1000 pulses, and the applied voltage may be approximately 300-4000 V. In one embodiment, as shown in FIG. 6, the pulse width may be set to 5 μs, the inter-phase delay may be 5 μs, the inter-pulse delay may be 800 μs, and the pulse train may include 80 pulses with an applied voltage of 700V. Such a pulse train when delivered from a bipolar electrode array (such as the array shown in FIG. 1) may produce lesions in cardiac muscle in the range of approximately 2-3 mm deep. Increased voltage may correspondingly increase the lesion depth. In an another configuration, four pulse trains may be delivered at each target tissue site and the pulse trains may be gated to start at the end of the S-wave of the sinus rhythm isoelectric line.

Figure 2:
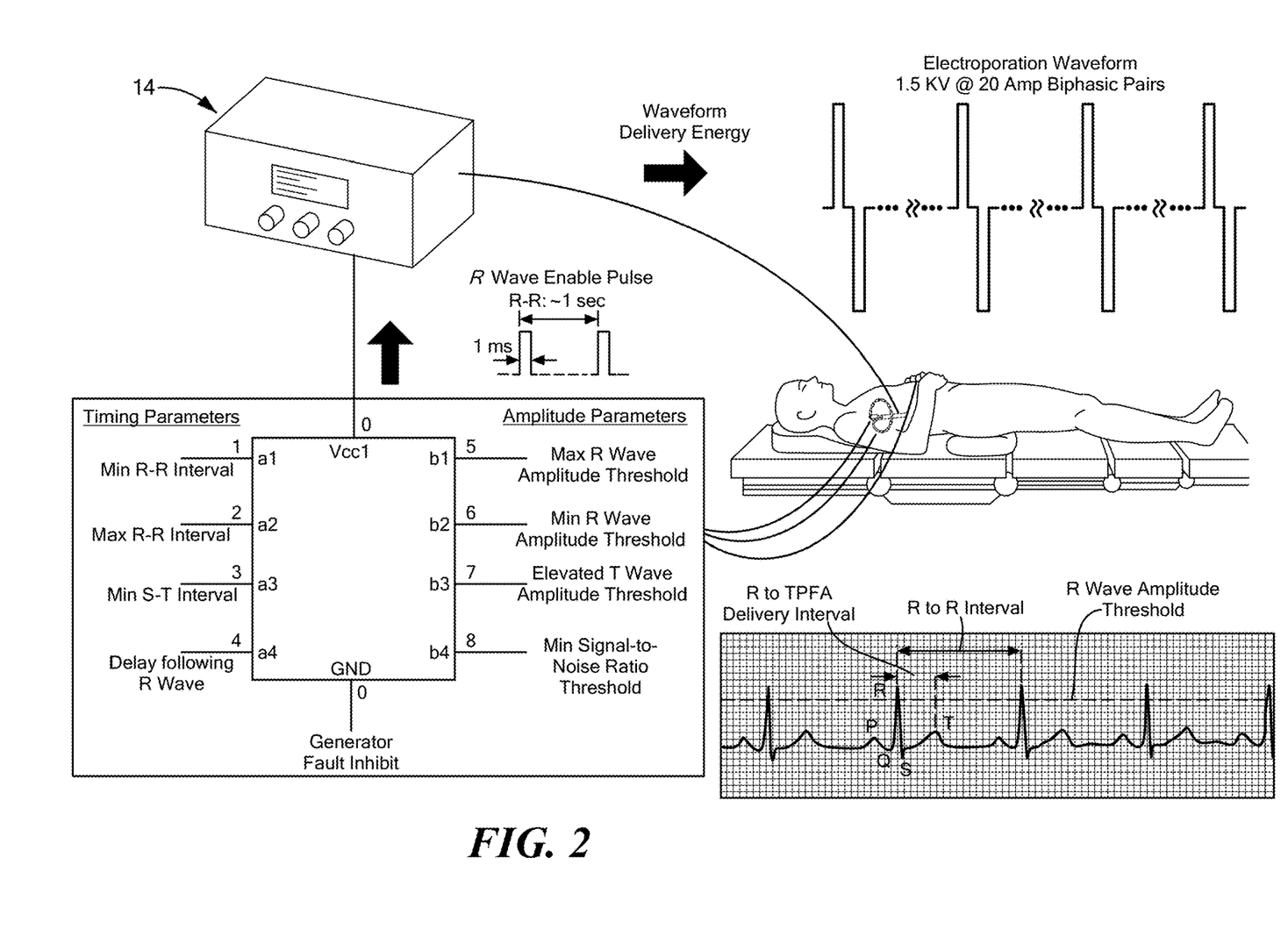
FIG. 2 shows an exemplary gated delivery system constructed in accordance with the principles of the present application.

Referring now to FIGS. 1 and 2, the system may include ECG electrodes 26 electrically couplable to the generator 14 and configured to measure electrical signals from the heart. The ECG measurements, or Einthoven signals, made by the ECG electrodes 26 may be sequentially or simultaneously made with the delivery of the pulse trains from the plurality of electrodes 24. In an exemplary configuration, three ECG electrodes 26 are adhered the surface of the patient and are further coupled to the generator 14. The generator 14 may include a second processor 32 configured to process and correlate the measured Einthoven signals into a determination of when to deliver pulses. For example, the second processor 32 may be programmed with predetermined measured patient parameters, for example, timing and amplitude parameters associated with a QRS wave, to gate the delivery of pulses to approximately 70-100 ms after the onset of an R-Wave. Such timing parameters may include a minimum R-R interval between adjacent QRS waves; a maximum R-R interval between adjacent QRS waves; the minimum S-T interval, and the desired delay following the onset of an R-wave. The amplitude parameters may include a maximum R-wave amplitude; a minimum R-wave amplitude, elevated T-wave threshold; and a minimum signal-to-noise ratio threshold. When at least one of the predetermined measured patient parameters are met, the second processor 32 communicates with the first processor 17 to initiate the delivery of pulses for a predetermined period of time.

The pulsed field of energy may be delivered in a bipolar fashion, between odd and even electrodes, in monophasic or biphasic pulses. The application of biphasic electrical pulses may produce unexpectedly beneficial results in the context of cardiac tissue ablation. With biphasic electroporation pulses, the direction of the pulses completing one cycle alternates in a few microseconds. As a result, the cells to which the biphasic electrical pulses are applied undergo alternation of electrical field bias. Changing the direction of bias reduces prolonged post-ablation depolarization and/or ion charging. As a result, prolonged muscle excitation (e.g., skeletal and cardiac cells) and risks of post shock fibrillation of the cardiac cells may be reduced. Further, biphasic electrical pulses may overcome the high impedance characteristics of fatty cells that are often problematic in cardiac ablation procedures.

Figure 3:
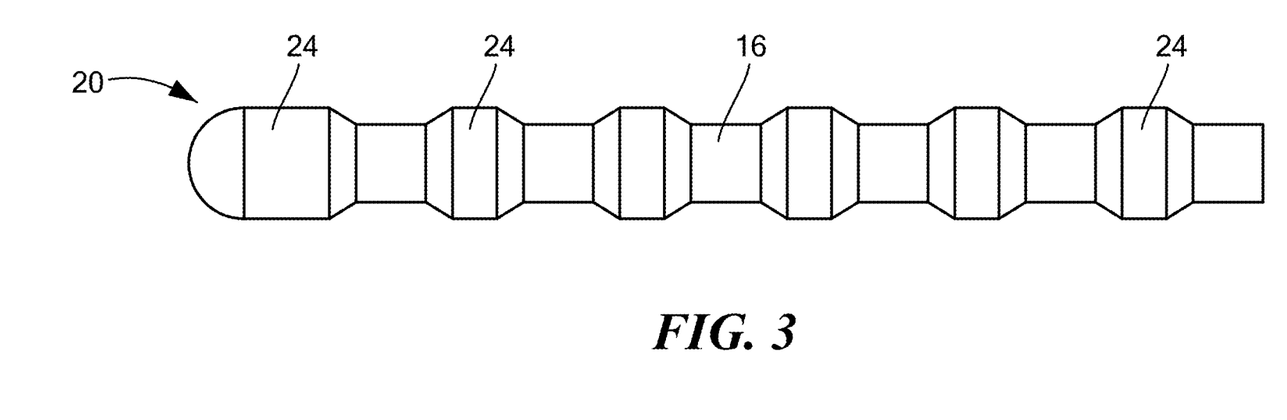
FIG. 3 shows a close-up view of an ablation device having an exemplary linear distal electrode array portion.
Figure 8:
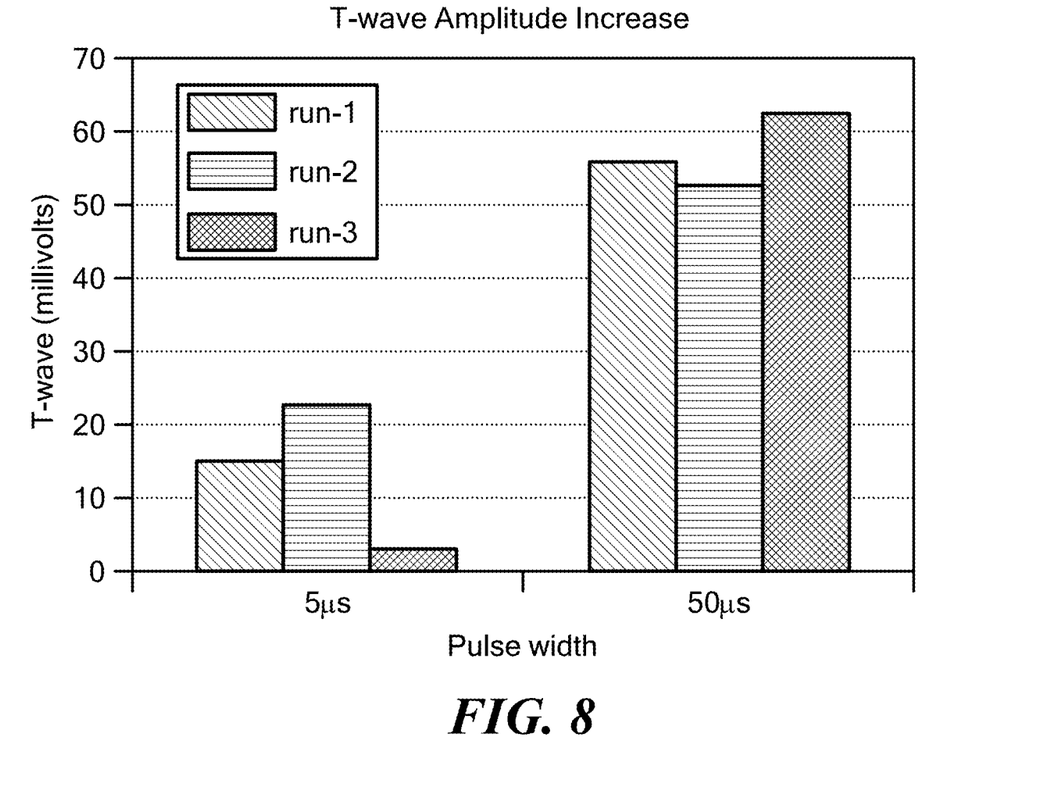
FIG. 8 shows the difference in effect of short (5 µs) and longer (50 µs) pulse widths on transient T-wave amplitude increases seen following pulse train delivery near the circumflex coronary artery.

Referring now to FIG. 3 in more detail, the pulse width B may be 5 μs or less, based at least in part on the evaluation of bubble output at high voltages and/or evidence of thermal effects on the tissue surface. As for the presence of bubbles, a pulse width of greater than 15 μs may be more likely to produce significant gas bubble volume and pulse widths of 20 μs or longer may produce thermal effects on the tissue surface. No loss of efficacy has been observed when going from 100 μs to 5 μs pulse width. Further, pulses with a pulse width as short as 5 μs may reduce nerve and skeletal muscle and blood vessel contraction (i.e. non-collateral tissue) stimulation. FIG. 8 compares the effect of 5 μs pulses to 50 μs pulses on coronary artery spasm. In three separate energy deliveries near the circumflex artery for both pulse widths, the 5 μs pulses caused substantially less T-wave amplitude increase compared to the 50 μs pulse width, which indicates that the shorter 5 μs pulses are advantageous. In an exemplary pulse delivery initiation procedure, the generator 14 is configured to initiate the pulse train of energy after a predetermined delay following the delivery of a 5-10V, low amplitude monophasic pacing pulse from the plurality of electrodes 24. The pacing pulse may have a duration of 0.01-2.0 ms and, in an exemplary configuration 0.5 ms in duration. In one configuration, the low amplitude monophasic pacing pulse is the last pulse in a series of pacing pulses delivered by the generator 14.

An applied voltage amplitude of between approximately 200V and approximately 300V may be the threshold amplitude at which irreversible damage is caused to myocardial cells that are in direct contact with the electrodes 24. Further, the delivery of pulse trains of 20 pulses or fewer at 200V produced brief reductions in electrogram amplitude (EGM), and delivery of the same pulse trains at 300V produced EGM amplitude reductions with more permanence. The delivery of the same pulse trains at 400V and at 500V produced permanent EGM amplitude reductions. Considering the bipolar electrode configuration in FIG. 1, electric field modeling indicated that the maximum electric field strength at an applied voltage of 300V at which cardiomyocyte death may occur is approximately 300-400V per centimeter. Moreover, delivery of 60 pulses per train, four trains per position, at 500V, 100 μs pulse width, 200 μs inter-phase duration, and 200 μs inter-pulse duration produced lesions that rivaled those produced by RF ablations, delivered as one minute of RF energy per site. The pulsed-field ablation deliveries produced larger EGM amplitude reductions than phased RF and more frequently produced transmural lesions and contiguous lesions with fewer sequestered viable myocytes than phased RF.

Figure 5:
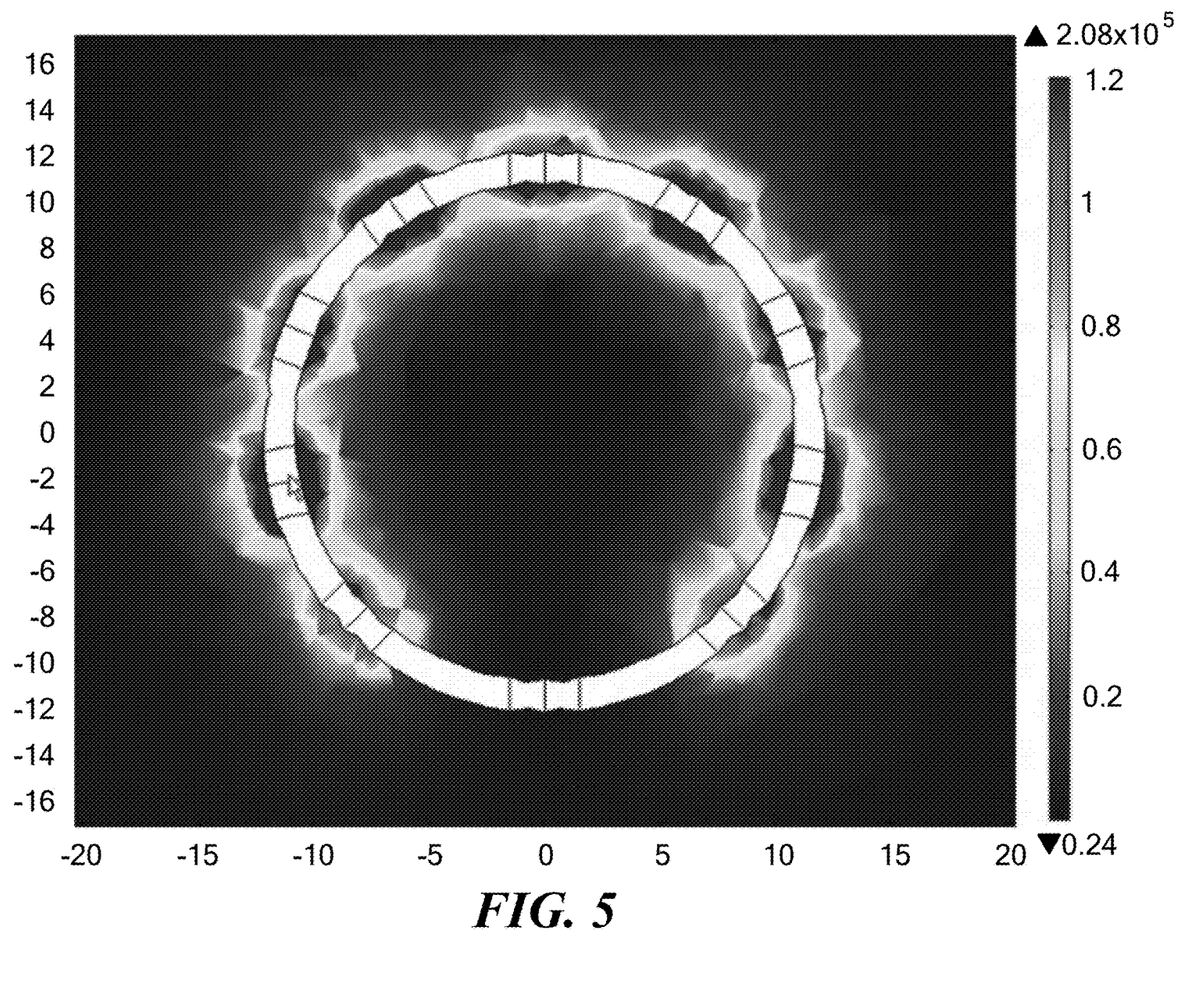
FIG. 5 shows an electric field distribution from the ablation device delivering pulsed energy during pulsed-field ablation.

In general, irreversible electroporative effects may be obtained if the E-field distribution is oriented such that the highest field strength is applied along (or parallel to) the long axis of the targeted cells. However, maximal irreversible electroporative effects may be achieved if multiple field vectors are applied to the targeted cells because different cells may react differently to a particular E-field orientation. An exemplary E-field is shown in FIG. 5, generated by the distal portion 20 shown in FIG. 1. In the distal portion 20 shown in FIG. 1, the polarity of adjacent electrodes 24 may be alternated to achieve the widest variety of field directions possible. If more than one vector is used, a larger percentage of cells may be affected and a more complete lesion may be created. Although not shown, additional distal portion 20 configurations may be used to produce a variety of E-field vectors. As a non-limiting example, the distal portion 20 may include a mesh-covered balloon, a balloon with embedded surface electrodes, or a splined basket with multiple electrodes. Additionally or alternatively, additional electrodes may be added to existing devices (for example, the PVAC ablation catheter sold by Medtronic, Inc., as shown in FIG. 1), such as on the central shaft or tip that could be used as counter electrodes to deliver some of the pulses to add a new field direction. Such deliveries may pass simultaneously from all of the PVAC electrodes to the separate electrode or from specific PVAC electrodes to the separate electrode.

Since effective pulsed-field RF ablation pulse trains can be delivered in a matter of tens of milliseconds, the energy may be delivered at specific points in the cardiac cycle where motion of the local heart wall causes the electrodes 24 to move slightly on the endocardial surface, such that each pulse train could impact a slightly different site on the heart wall. This technique may be used to distribute a lesion over a broader area. Further, it may allow for precise energy delivery at only the intended site if that moment in the cardiac cycle is chosen for delivery. The length of a pulse train may have a similar effect: short pulse trains may target a smaller area whereas longer trains may be more likely to affect a broader area.

Higher quality lesions may be created with a larger number of pulses in the pulse train. However, long pulse trains may be so long from first to last pulse that the last pulse may enter the time frame of the vulnerable period of the T-wave. Larger numbers of pulses could be added if the inter-phase and inter-pulse durations were decreased, but this may cause excess heating of the electrodes, which may be undesirable. To avoid heating, an inter-pulse duration of at least approximately 400 µs may be used, which may allow for 80 pulses (10 µs pulse width) to be delivered in an acceptable time window that avoids entry into the T-wave. Although this assumes that there is concern over induction of ventricular fibrillation (VF), VF may not be a concern when ablating in the pulmonary vein ostial and pulmonary vein antral regions.

Inter-phase and inter-pulse durations have been evaluated in terms of their effect on lesion formation, and bubble formation. These studies indicated that keeping the inter-phase duration as short, for example 5 µs, did not produce any disadvantage in terms of lesion creation efficacy. As is shown in FIG. 6, the pulse train may include 80 pulses, a 65.2 ms pulse train duration (0.8 ms "ON time"), a 5 µs inter-phase delay, am 800 µs inter-pulse delay, and a 5 µs pulse width. However, reducing the pulse cycle length may allow the frequency to be increased to a point where nerve and skeletal muscle stimulation is not produced. Although this may produce one or more of the plurality of electrode 24s overheating and bubble production if more pulses are added, the pulse cycle length may be reduced to increase frequency using short pulses. As long as the frequency and total number of pulses is below the threshold of significant bubble formation, the increased frequency may reduce or eliminate muscle and nerve stimulation.

Figure 7:
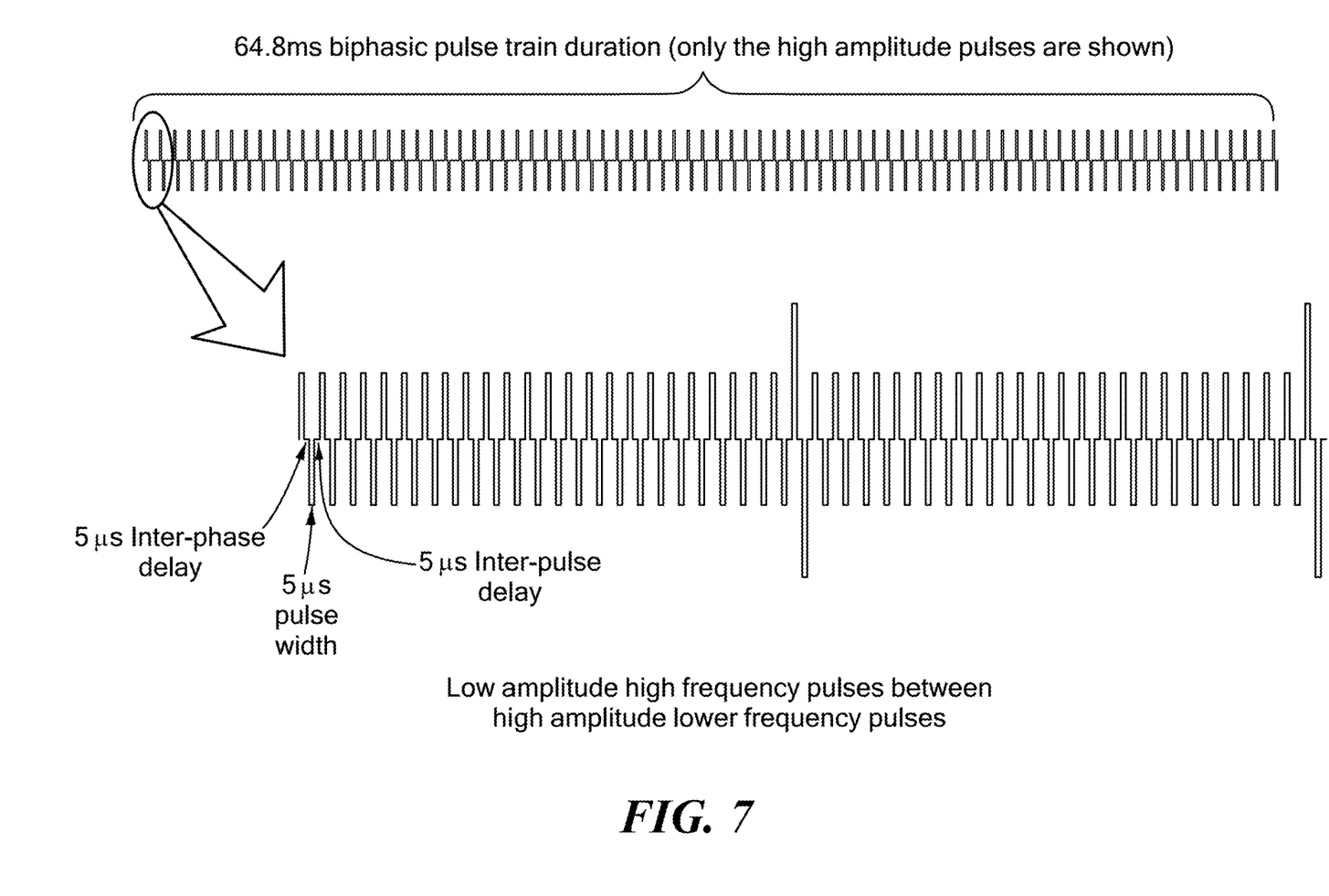
FIG. 7 shows a pulsed-field ablation pulse train with a 5 µs inter-phase delay, a 5 µs pulse width, and a 5 µs inter-pulse delay, and including both low-amplitude, high-frequency pulses and high-amplitude, lower-frequency pulses.

In another example, the pulse train shown in FIG. 7 may include 80 high-amplitude therapeutic pulses with high-frequency, lower amplitude pulses being delivered between each of the high-amplitude, lower-frequency pulses. This example provides a 50 kHz frequency that exceeds the frequency of tetanic muscle contraction and provides for less discomfort during delivery. The low amplitude pulses may have an amplitude which is below the threshold of causing electroporative effects on the tissue but it is of high enough amplitude to excite muscle and nerves in the tissue. In this way a high frequency pulse train may be delivered while minimizing both muscle stimulation and excess delivery of electrical current.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device comprising a generator in electrical communication with a plurality of electrodes, wherein the generator is configured to deliver a pulse train of energy having a predetermined frequency and including a plurality of pulses, each pulse having a pulse width of between 1 µs and 15 µs, wherein the plurality of pulses includes a sequence of alternating positive pulses and negative pulses with an inter-phase delay after each positive pulse and before a subsequent negative pulse and with an inter-pulse delay after each negative pulse and before a subsequent positive pulse, wherein the inter-phase delay is less than the inter-pulse delay.

2. The medical device of claim 1, wherein the generator comprises at least one processor configured to control the delivery of the pulse train of energy based upon a measured patient parameter.

3. The medical device of claim 1, wherein the generator is configured to deliver the pulse train of energy in a bipolar mode via the plurality of electrodes wherein when the pule train of energy is delivered in a bipolar mode, each electrode has a polarity that is different from the polarity of each adjacent electrode.

4. The medical device of claim 2, further comprising a plurality of ECG electrodes configured to be coupled to the generator and in communication with the at least one processor, the plurality of ECG electrodes being configured to measure at least one electrical waveform generated by a patient's heart, and wherein the measured patient parameter is measured by the plurality of ECG electrodes.

5. The medical device of claim 1, wherein the inter-phase delay is between 0 µs and 5 µs, and wherein the inter-pulse delay is at least 400 µs.

6. The medical device of claim 5, wherein the pulse train of energy further comprises at least 20 positive pulses and at least 20 negative pulses.

7. The medical device of claim 6, wherein the pulse train of energy further includes a voltage between 300V and 2000V and wherein the predetermined frequency is approximately 1 kHz.

8. The medical device of claim 1, wherein the pulse train of energy is configured to be delivered between 70 ms and 100 ms after an onset of an R-wave of a patient's heart.

9. The medical device of claim 1, wherein the pulse train of energy is configured to be delivered after an end of an S-wave of a patient's heart.

10. A method of ablating cardiac tissue, the method comprising delivering a pulse train of energy having a predetermined frequency to a cardiac tissue, the pulse train of energy including a plurality of pulses, each pulse having a pulse width of between 1 µs and 15 µs, and an inter-pulse delay of at least 400 µs, wherein the plurality of pulses includes a sequence of alternating positive pulses and negative pulses with an inter-phase delay after each positive pulse and before a subsequent negative pulse and with the inter-pulse delay after each negative pulse and before a subsequent positive pulse, wherein the inter-phase delay is less than the inter-pulse delay.

11. The method of claim 10, wherein the pulse train of energy further comprises at least 20 positive pulses and at least 20 negative pulses.

12. The method of claim 11, wherein the inter-phase delay is between 0 µs and 5 µs.

13. The method of claim 12, wherein the pulse width is between 1 µs and 5 µs.

14. The method of claim 13, wherein the delivering a pulse train of energy comprises delivering the pulse train of energy between 70 ms and 100 ms after an onset of an R-wave of a patient's heart.

15. The method of claim 10, wherein the predetermined frequency is less than 3 kHz.

16. The method of claim 10, the method further comprising
delivering a plurality of pulse trains of energy to a plurality of cardiac treatment sites.

17. A system for ablating cardiac tissue, the system comprising:
a generator configured to deliver at least one pulse train of energy at a predetermined frequency, each pulse train of energy having a plurality of pulses, each pulse having a pulse width of between 1 µs and 15 µs and an inter-pulse delay of at least 400 µs, the generator including at least one processor configured to control the delivery of the at least one pulse train of energy based on a measured patient parameter, wherein the plurality of pulses includes a sequence of alternating positive pulses and negative pulses with an inter-phase delay after each positive pulse and before a subsequent negative pulse and with the inter-pulse delay after each negative pulse and before a subsequent positive pulse, wherein the inter-phase delay is less than the inter-pulse delay.

18. The system of claim 17, further comprising a controller configured to be communicatively coupled to one or more ECG electrodes and configured to detect the onset of an R-wave, wherein the measured patient parameter includes the detection of the onset of the R-wave, and wherein the generator is configured to initiate the pulse train of energy between 70 ms and 100 ms after the onset of the R-wave.

* * * * *